United States Patent
Li (10) Patent No.: US 10,156,494 B2
(45) Date of Patent: Dec. 18, 2018

(54) TESTING EQUIPMENT OF ONBOARD AIR CONDITIONING SYSTEM AND A METHOD OF TESTING THE SAME

(71) Applicant: Air China Limited, Beijing (CN)

(72) Inventor: Qixiang Li, Beijing (CN)

(73) Assignee: Air China Limited, Airport Industrial Zone, Shunyi District, Beijing (CN)

( * ) Notice: Subject to any disclaimer, the term of this patent is extended or adjusted under 35 U.S.C. 154(b) by 51 days.

(21) Appl. No.: 14/957,159

(22) Filed: Dec. 2, 2015

(65) Prior Publication Data

US 2016/0157034 A1 Jun. 2, 2016

(30) Foreign Application Priority Data

Dec. 2, 2014 (CN) .......................... 2014 1 07208602

(51) Int. Cl.
  *G01N 29/14* (2006.01)
  *G01M 7/00* (2006.01)
  *G01N 29/46* (2006.01)

(52) U.S. Cl.
  CPC .............. *G01M 7/00* (2013.01); *G01N 29/14* (2013.01); *G01N 29/46* (2013.01)

(58) Field of Classification Search
  CPC ......... G01M 7/00; G01N 29/14; G01N 29/46; G01N 2291/2696; G01N 2291/015
  USPC .................... 73/658, 659, 661, 593
  See application file for complete search history.

(56) References Cited

U.S. PATENT DOCUMENTS

| | | | |
|---|---|---|---|
| 6,370,957 B1 | 4/2002 | Filippenko et al. | |
| 6,725,705 B1* | 4/2004 | Huebler | G01M 3/243 |
| | | | 702/51 |
| 2003/0196492 A1 | 10/2003 | Remboski et al. | |
| 2005/0046584 A1* | 3/2005 | Breed | B60C 11/24 |
| | | | 340/13.31 |
| 2008/0147270 A1* | 6/2008 | Sakane | B60H 1/00864 |
| | | | 701/36 |
| 2008/0294430 A1* | 11/2008 | Ichikawa | G10L 21/0208 |
| | | | 704/226 |

(Continued)

FOREIGN PATENT DOCUMENTS

| | | |
|---|---|---|
| CN | 102023098 A | 4/2011 |
| CN | 104033993 A | 9/2014 |
| EP | 1 850 325 A1 | 10/2007 |

OTHER PUBLICATIONS

Extended European search report from the European Patent Office for counterpart European Application No. EP 15 197 648.7 dated May 9, 2016.

(Continued)

*Primary Examiner* — Manish S Shah
*Assistant Examiner* — Rose M Miller
(74) *Attorney, Agent, or Firm* — Finnegan, Henderson, Farabow, Garrett & Dunner LLP (57) ABSTRACT

A testing equipment of an airplane air conditioning system is disclosed. The test equipment includes a sound receiver and a sound processor. The sound processor processes running noise of airplane air conditioning system sampled by the sound receiver to assess the operative condition of the system. The sound receiver samples environmental noise when the airplane air conditioning system is not running, and the sound processor de-noises the running noise by using the environmental noise.

18 Claims, 3 Drawing Sheets

(56) References Cited

U.S. PATENT DOCUMENTS

2010/0094633 A1* 4/2010 Kawamura ............. G10L 15/02
　　　　　　　　　　　　　　　　　　　　　　　704/270
2016/0006576 A1* 1/2016 Matsuzaki ............. G06F 13/00
　　　　　　　　　　　　　　　　　　　　　　　709/224

OTHER PUBLICATIONS

First Chinese Search Report issued in Chinese Application No. 201510875680.6, dated Sep. 12, 2018 (2 pages).

\* cited by examiner

TESTING EQUIPMENT OF ONBOARD AIR CONDITIONING SYSTEM AND A METHOD OF TESTING THE SAME

TECHNICAL FIELD OF THE INVENTION

The present invention relates to the field of aerotechnics. Specifically, it involves testing equipment of an onboard air conditioning system and a method of testing the same.

BACKGROUND

As a key contributing factor to the comfort of air passengers, onboard air conditioning system needs to be tested from time to time in the routine maintenance, especially when complaints arise to its performance by the aircrew, to ensure it works well.

The direct approach to test the performance of onboard air conditioning in the prior art is to acquire the temperature of each key position within the system and then determine its running condition by drawing a reverse Karnaugh map or using a differential method. That being said, temperature measurement is merely an ideal testing method as it requires the mounting of temperature sensors and electric power circuits and/or signal transmission lines at the key positions of onboard air conditioning system. In practicality, however, the tubes for key positions in the onboard air conditioning system are arranged in such complexity that they render the measurement points nearly inaccessible, resulting in a low possibility to obtain an accurate and standard measurement results. Also, the temperature sensors per se require maintaining, which, together with the hardly possible arrangement for a temperature acquisition system, makes the temperature measurement approach fail to receive a widespread application among airline companies.

Such being the case, testing the performance of an onboard air conditioning system conveniently has always been a problem facing the airline industry.

SUMMARY

In response to the technical problem above, the present application provides testing equipment of onboard air conditioning systems, comprising a sound receiver and a sound processor, wherein the sound processor processes the running noise of an onboard air conditioning system sampled by the sound receiver to assess the operative condition of the system.

The equipment as described above, wherein the sound receiver is an independent microphone or a built-in microphone.

The equipment as described above, wherein the sound receiver is mounted at the air outlet of the onboard air conditioning system or in the cabin.

The equipment as described above, wherein the sound receiver samples the environmental noise when the onboard air conditioning system is not running.

The equipment as described above, wherein the sound processor de-noises the running noise by using environmental noise.

The equipment as described above, wherein the sound processor determines a change in the running noise by comparing the running noise with the standard noise of the onboard air conditioning system.

The equipment as described above, wherein the sound processor assesses the failure source of the onboard air conditioning system.

The equipment as described above, wherein the sound processor assesses the failure cause of the onboard air conditioning system.

The equipment as described above, wherein the sound processor analyzes the waveform and/or frequency spectrum of the running noise of onboard air conditioning system and extracts the waveforms and/or frequency spectrums of noises corresponding to different devices in the onboard air conditioning system.

The equipment as described above, wherein the sound processor determines the failure source or failure cause by a combined use of the waveforms and/or frequency spectrums of noises of a plurality of devices.

The equipment as described above, wherein the sound processor assesses whether the devices in the onboard air conditioning system are in a deterioration period.

The equipment as described above, wherein the sound processor compares the running noise with the history noises of the onboard air conditioning system.

The equipment as described above, wherein the sound processor assesses whether the device is in a deterioration period by analyzing the change in the variation trend of waveforms and/or frequency spectrums of the running noises of one or more devices in the onboard air conditioning system.

The equipment as described above, wherein the sound processor assesses the time of failure of the device.

According to the other aspect of the present invention, it provides a method of testing the onboard air conditioning system, comprising: sampling the running noise of onboard air conditioning system and assessing the operative condition of onboard air conditioning system.

The method as described above, further comprises sampling the environmental noise when the onboard air conditioning system is not running.

The method as described above, further comprises denoising the running noise by using environmental noise.

The method as described above, further comprises determining a change in the running noise by comparing the running noise with the standard noise of the onboard air conditioning system.

The method as described above, further comprises assessing the failure source of the onboard air conditioning system.

The method as described above, further comprises assessing the failure cause of the onboard air conditioning system.

The method as described above, further comprises analyzing the waveform and/or frequency spectrum of the running noise of onboard air conditioning system, and extracting the waveforms and/or frequency spectrums of noises corresponding to different devices in the onboard air conditioning system.

The method as described above, further comprises determining the failure source or failure cause by a combined use of the waveforms and/or frequency spectrums of noises of a plurality of devices.

The method as described above, further comprises assessing whether the devices in the onboard air conditioning system are in a deterioration period.

The method as described above, further comprises comparing the running noise with the history noises of onboard air conditioning system.

The method as described above, further comprises assessing whether the device is in a deterioration period by analyzing the change in the variation trend of waveforms and/or frequency spectrums of the running noises of one or more devices in the onboard air conditioning system.

The method as described above, further comprises assessing the time of failure of the device.

BRIEF DESCRIPTION OF THE DRAWINGS

Hereinafter, some preferred embodiments of the invention will be described in reference to the accompanying drawings.

DETAILED DESCRIPTION OF THE INVENTION

To understand the objects, technical solutions and advantages of the Examples more clearly, the technical solutions of the Examples are defined explicitly and completely below based on the Figures in the Examples of the present invention. The Examples described are only a part of, not exhaustive, examples of the present invention. On the basis of the Examples, all examples obtained by a person skilled in the art without involving creative work fall under the protection scope of the present invention.

Compared with civilian onboard air conditioning systems, the present invention differs in that there is no application of refrigerant. The onboard air conditioning of the present application provides air of high temperature and high pressure, as working and cooling media, for the onboard air conditioning system by directly using aeromotor air entraining, APU air entraining or an independent compressor. Thanks to the absence of refrigerant, the cooling effect provided by the onboard air conditioning system is greatly enhanced.

Figure 1:
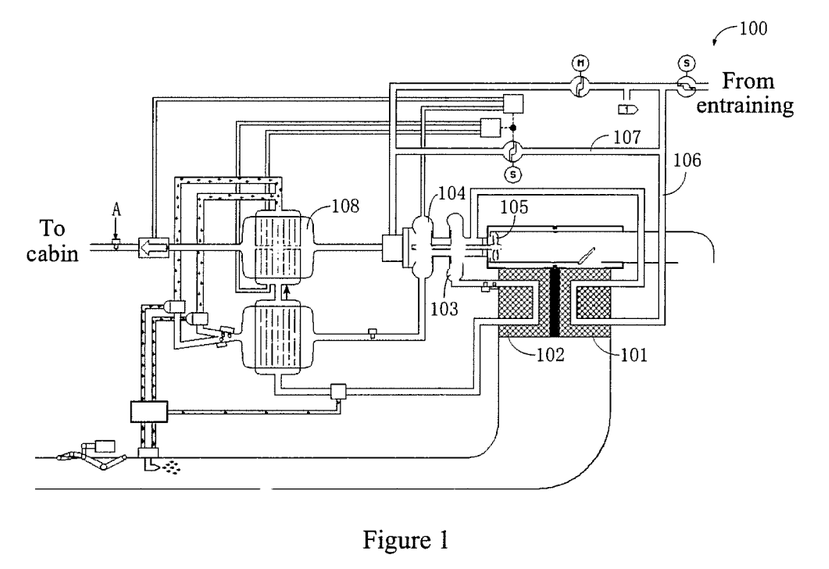
FIG. 1 is a schematic diagram showing the structure of onboard air conditioning system in an airplane.

FIG. 1 is a schematic diagram showing the structure of a typical three-wheel onboard air conditioning system. As illustrated in FIG. 1, the onboard air conditioning 100 comprises primary heat exchanger 101, secondary heat exchanger 102, compressor 103 and turbine 104. For the purpose of increasing the operating efficiency of the system in such working conditions as ground, the onboard air conditioning system further comprises a fan 105.

The air of high temperature and high pressure, e.g. from aeromotor, is transported along gas pipelines 106 and 107, respectively. The air in the pipeline 106 firstly passes through the primary heat exchanger 101 that reduces its temperature and pressure, and again it becomes high in temperature and pressure after compressed in compressor 103. The air enters into the secondary heat exchanger 102 where it is lowered in temperature and pressure. Then, in the turbine 104, the air experiences a further substantial drop in temperature (as low as 10 degrees below zero) and pressure as a result of adiabatic expansion and turns into cooling gas. The cooling gas, after mixed with the air of high temperature from the pipeline 107, becomes air with a moderate temperature that is dehumidified by water separator 108 before going into the cabin.

According to an example of the present invention, the temperature of the air outlet (position A as shown in FIG. 1) of the cabin is measured to determine the overall performance of onboard air conditioning system. In spite of its simplicity, the method could only measure the performance of the system, failing to find out its fault localization. That means the method can be used as a supplement or pre-testing method of the testing method of onboard air conditioning in the present invention.

Figure 2:
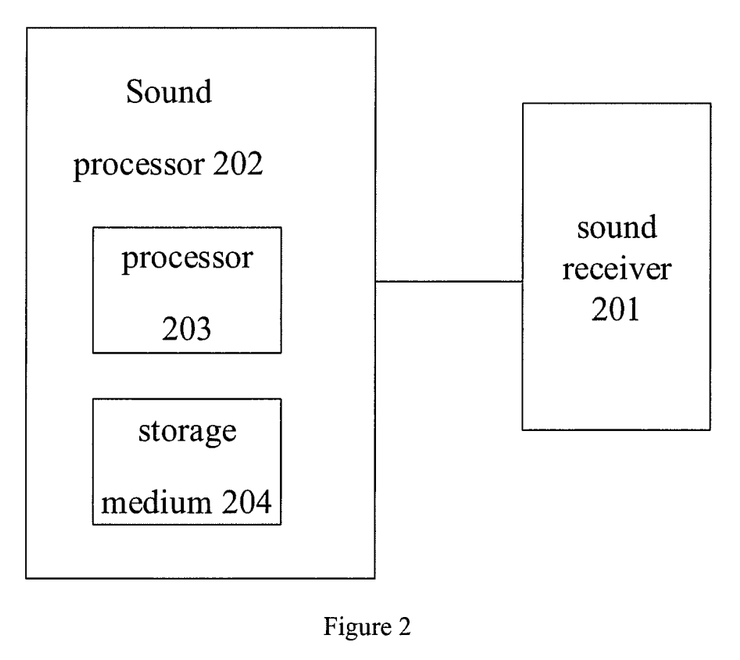
FIG. 2 is a schematic diagram showing the structure of the testing equipment of onboard air conditioning system in an example based on the present invention.

FIG. 2 is a schematic diagram showing the structure of the testing equipment of onboard air conditioning system in an example based on the present invention. As shown in FIG. 2, the testing equipment 200 of the onboard air conditioning system comprises sound receiver 201 and sound processor 202. The sound receiver 201 receives the running noise of the onboard air conditioning system. The sound processor 202 processes the running noise of the onboard air conditioning system received by the sound receiver 201 to determine the operative condition of the system. According to an example of the present invention, the sound processor 202 determines the failure source when the onboard air conditioning system goes wrong.

According to an example of the present invention, the sound processor 202 analyzes the waveform and/or frequency spectrum of the running noise of the onboard air conditioning system, determining the performance and/or failure source of the onboard air conditioning system based on changes in waveforms and/or frequency spectrums.

In one example, sound processor 202 compares the waveforms and/or frequency spectrums of running noise of the onboard air conditioning system received by sound receiver 201 with those of the properly-functioned onboard air conditioning system, i.e. standard waveforms and/or frequency spectrums of noise, to determine the changes in waveforms and/or frequency spectrums. For example, the waveforms and/or frequency spectrums of running noise of the properly-functioning onboard air conditioning system come from the onboard air conditioning system in the same airplane, which is recently installed or has been properly functioning for a predetermined period of time, or are the waveforms and frequency spectrums in theory or mean-processed.

According to an example of the present invention, the sound processor 202 analyzes the waveform and/or frequency spectrums of the running noise of the onboard air conditioning system, and extracts the waveforms and/or frequency spectrums of noises corresponding to different devices in the onboard air conditioning system. On the basis of the changes in the waveforms and/or frequency spectrums of noises corresponding to the devices, the failure source can be determined. For example, the air flow noise produced as air flow passes through the heat exchanger has a greatly different frequency from the noise of a compressor. As another example, the noise frequency of the compressor arises resulting from its accelerated running speed when the heat exchanger is blocked. Meanwhile, the failure of the compressor per se tends to decelerate its running speed, which, in turn, brings down the noise frequency. As such, the failure source, whether from a heat exchanger or a compressor, can be determined based on the change in the noise frequency of the compressor.

According to an example of the present invention, the changes in waveform and/or frequency spectrum of the noise arising from rupture of the blade and bearing wear of the same apparatus, e.g. compressor, are different. The rupture of the blade reduces the noise frequency of the compressor and increases waveform amplitude, while the bearing wear lowers the noise frequency of the compressor and brings about new high-frequency noise in the high-frequency areas simultaneously. In this connection, the changes in the waveform and/or frequency spectrum of noise corresponding to the device of onboard air conditioning system is useful in determining both the failure source and the failure cause.

According to an example of the present invention, the failure source and failure cause can be determined by a combined use of changes in the waveform and/or frequency spectrum of noises of a plurality of devices in the onboard air conditioning system.

According to an example of the present invention, the sound receiver 201 samples the environmental noise when the onboard air conditioning system is not running. The sound processor 202 removes the environmental noise from the running noise of onboard air conditioning system through a reverse superposition of the running noise and the environmental noise of the idle system, thereby minimizing the environmental noise.

The noise in the onboard air conditioning system mainly comes from turbine, compressor and fans. Due to their difference, the three devices each have their own distinctive waveforms and frequency spectrums during the running of the system. After the removal of environmental noise, however, it is easy to differentiate the distinctive waveforms and frequency spectrums of noises of the three devices from the remaining waveforms and spectrums of noises. Also, the changes in the distinctive waveforms and spectrums of noises of the turbine, compressor and fans can be determined readily through a comparison between the distinctive waveforms and frequency spectrums of the noises of the three devices and the ones of standard turbine, compressor and fans. Specifically, the spectrum obtained from a reverse superposition of the distinctive waveforms and spectrums of noises of the turbine, compressor and fans with these of standard turbine, compressor and fans shows the changes in the distinctive waveforms and frequency spectrums of noises of the turbine, compressor and fans.

As described above, the distinctive waveforms and frequency spectrums of noises of the standard turbine, compressor and fans come from the onboard air conditioning system that is recently installed or has been properly functioning for a predetermined period in the same airplane. Of course, the distinctive waveforms and frequency spectrums of noises are also applicable, which come from the onboard air conditioning system recently installed or properly functioning for a predetermined period in other airplanes of the same type or are in theory or mean-processed. Having said that, the distinctive waveforms and frequency spectrums of noises of standard turbine, compressor and fans coming from the same airplane are more accurate.

According to an example of the present invention, the sound receiver 201 comprises a microphone, a microphone with de-noising function in particular. For instance, the microphone can be an ordinary, independent microphone; a built-in microphone in a device, such as the built-in microphone in a laptop; a condenser microphone capable of capturing audio within a wider range; or a microphone able to function well in a test site with harsh conditions. According to an example of the present invention, the sound receiver 201 comprises two or more microphones.

According to an example of the present invention, the sound processor 202 can be a hardware circuit. According to an example of the present invention, the sound processor 202 comprises a processor 203 or other processing devices. Specifically, the sound processor 202 may comprise a processor, DSP, an application-specific integrated circuit (ASIC), FPGA or other programmable logic devices, dispersing door, or transistor logic, dispersing hardware element or any combination thereof that are designed to implement the function as described in the present invention. The processor can be a microprocessor but, in an alternative solution, it also can be any ordinary processor, controller, microcontroller or state machine. Additionally, the processor may be a combination of calculating devices, e.g. a combination of DSP and a microprocessor, a combination of microprocessors, a combination of one or more microprocessors and DSP core, etc.

The sound processor 202 comprises storage medium 204 that comprises random access memory (RAM), flash memory, read-only memory (ROM), electrically programmable read-only-memory ROM (EPROM), electrically erasable programmable read-only memory ROM (EEPROM), register, hard disk, loadable and unloadable disk, CD-ROM or any other computer readable medium known in the prior art. The coupling between storage medium and processor enables the processor to load information therefrom and write information thereinto. In an alternative solution, the store medium may be integrated with the processor.

According to an example of the present invention, the sound receiver 201 and sound processor 202 can be two independent devices conducting a wire or wireless communication. The sound receiver 201, for an unidirectional communication, sends the received noise signal to the sound processor 202, and, in case of a bidirectional communication, is commanded to work or stop by the sound processor 202 or is woken up and switched into a dormant state by the sound processor 202.

According to an example of the present invention, the sound receiver 201 is a wireless microphone while the sound processor 202 may be a dedicated device, e.g. a handheld device, comprising the processor and storage medium above. Further, the sound processor 202 can be a laptop, a tablet PC, a mobile phone, FDA, a personal computer, a server or another general device. Alternatively, such a general device is able to become a dedicated device that tests the onboard air conditioning by performing the function procedure codes of the sound processor 202. The wireless microphone communicates with the sound processor through Bluetooth, infrared, Wifi, WLan and other wireless communication modes.

According to an example of the present invention, the wireless microphone, as the sound receiver 201, is mounted on the air outlet (position A as shown in FIG. 1) of onboard air conditioning or any position in the cabin near to the onboard air conditioning, or any other predetermined position (please specify such a position). In the best case, the position is the one where the noise of the standard onboard air conditioning system is obtained.

According to an example of the present invention, the sound receiver 201 is integrated with the sound processor 202. For example, the sound processor 202 may be a laptop while the sound receiver 201 is a built-in microphone within the sound processor 202. Alternatively, the testing equipment 200 of the onboard air conditioning system is a handheld device comprising a built-in microphone, a processor and a storage medium.

Figure 3:
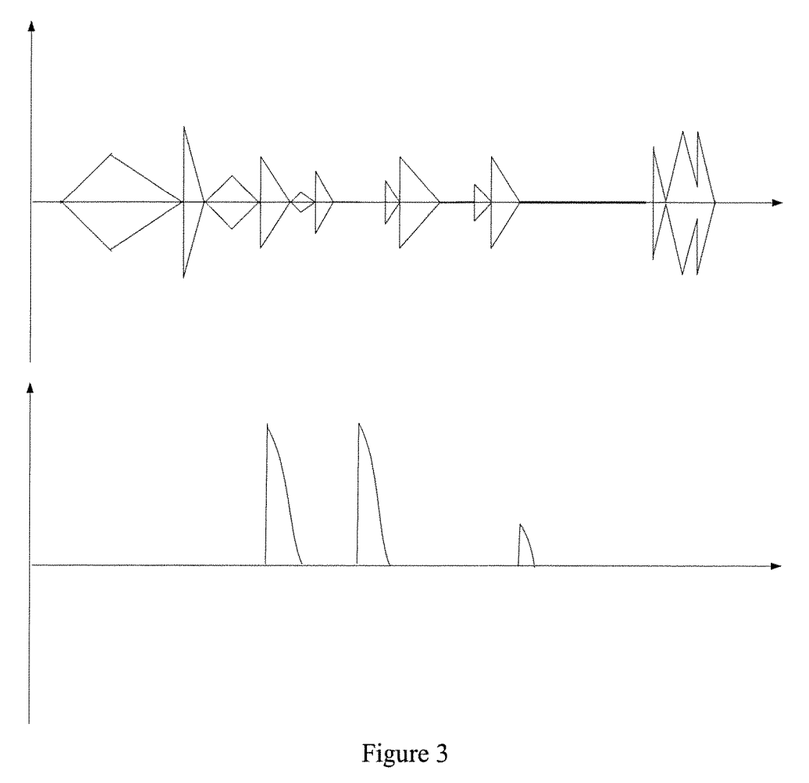
FIG. 3 is an exemplary graph of the changing curve of the performance of onboard air conditioning system.

FIG. 3 graphs the changing curve of the performance of the onboard air conditioning system. With the increase in hours of use, there will be a performance reduction in all onboard air conditioning systems, or steady growth in deterioration index. The performance of the onboard air conditioning system maintains a stale level when the deterioration index nearly experiences no change, begins to deteriorate when the deterioration index increases, and undergoes a failure period and breaks down from time to time when the deterioration index passes a specific threshold value. Once in failure period, the onboard air conditioning system may either provide undesirable service or bring about unexpected maintenance that causes flight delay and cancellation. In the prior art, there is no method available to determine whether the onboard air conditioning system enters into a deterioration period, which, however, is made possible by some examples in the present invention.

According to an example of the present invention, the sound processor 202 analyzes the change in noise of the onboard air conditioning system within a specific time period. On this basis, it determines whether the onboard air conditioning is in a stable period, or a deterioration period or a failure period. Further, the possible time for the malfunction of the onboard air conditioning system can be determined if the system is in a deterioration period. A plurality of approaches are helpful in finding out whether the onboard air conditioning system has entered into a deterioration period from a stable one. For example, such a detection can be made by observing the variation trend of the distinctive waveform or frequency of a device of the onboard air conditioning system. If there is a sudden change in the variation trend, e.g. a unforeseen increase in amplitude or frequency, the device has very likely been in a deterioration period.

The present invention uses a method to test the waveform and/or frequency spectrum of the running noise of the onboard air conditioning system, which is, conveniently and economically, able to test its performance without any link therebetween. Since each device within the system has a distinctive waveform and frequency of running noise, the testing method of the present invention can not only test the overall performance of the system but also find the exact device in failure or deterioration.

Figure 4:
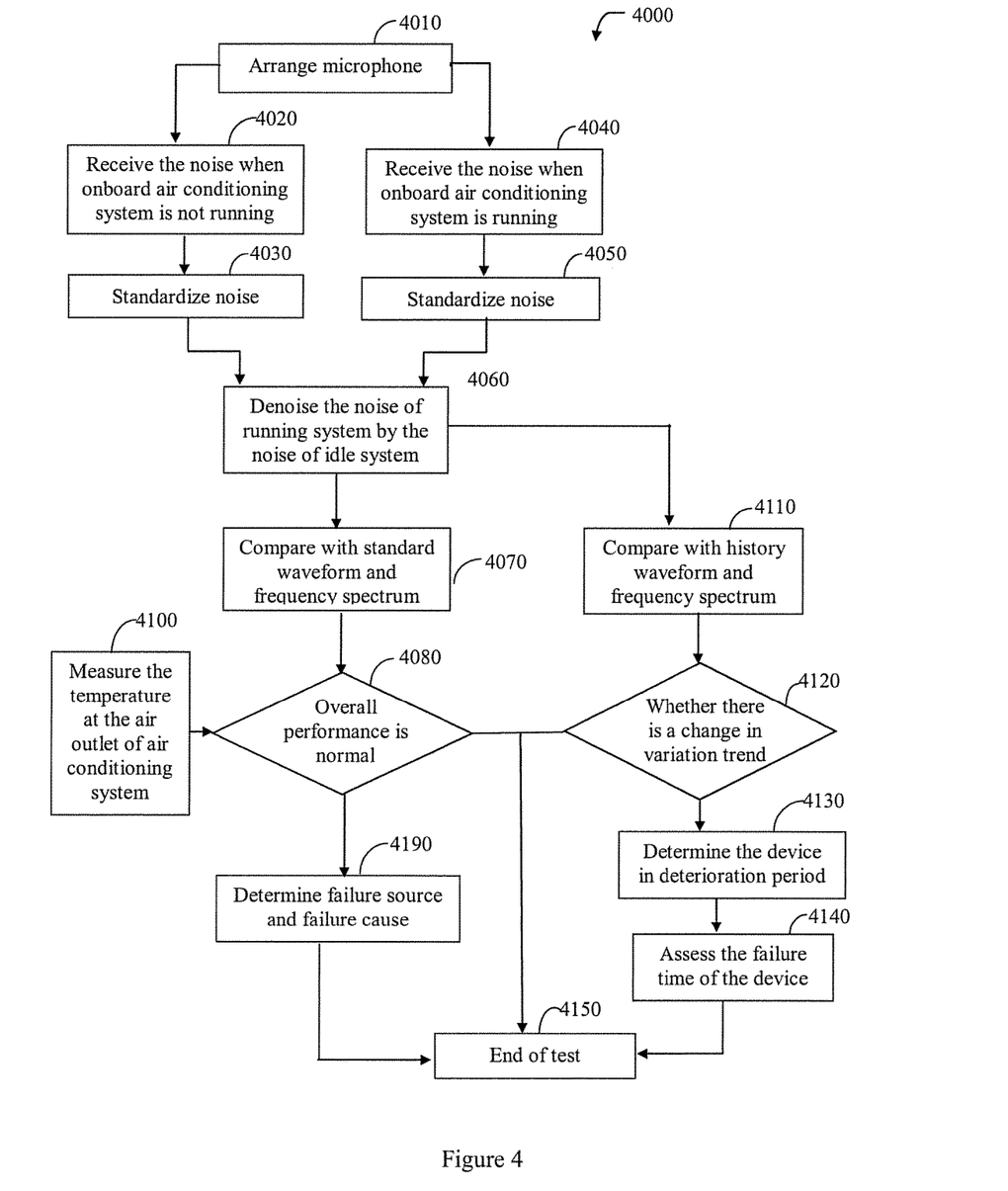
FIG. 4 is a flow chart showing the method of testing the onboard air conditioning system in an example based on the present invention.

FIG. 4 is a flow chart showing the method of testing the onboard air conditioning system in an example based on the present invention. The testing method 4000 comprises mounting a microphone for receiving the noise of the onboard air conditioning system in step 4010. For example, the microphone can be mounted at the air outlet of the system. If possible, it can also be mounted within the onboard air conditioning system, e.g. a position near compressor and heat exchanger. To facilitate the test, the microphone may be mounted at a position in the cabin in the proximity of the air conditioning system as described above.

In step 4020, the microphone receives the environmental noise when the onboard air conditioning system is not running. The received environmental noise may be stored in the storage medium. For example, the recorded audio file can be saved as a standard way or MP3 file. For example, the recorded time may have a length in a range of 5-10 seconds or 3-6 minutes. The sampling software used for the environmental noise can be such ordinary software as ADOBE® Audition or other professional software. Next, in step 4030, the received environmental noise is standardized, i.e. an unified audio level. As such, each test result has a corresponding standard reference, making the comparison between the follow-up waveforms and/or frequency spectrum and the standard or history ones possible.

Likewise, in step 4040, the microphone receives the noise of the running onboard air conditioning system. The received environmental noise may be stored in the storage medium. For example, the recorded audio file can be saved as a standard way or MP3 file. For example, the recorded time may have a length in a range of 5-10 seconds or 3-6 minutes. The sampling software used for the environmental noise can be such ordinary software as ADOBE® Audition or other professional software. Next, in step 4050, the received environmental noise is standardized, i.e. a unified audio level. As such, each test result has a corresponding standard reference, making the comparison between the follow-up waveforms and/or frequency spectrums and the standard or history ones possible.

The skilled in the art should understand that there is no particular order between 4020 and 4030 and 4040 and 4050. In other words, there is no particular sampling order between environmental noise and noise of onboard air conditioning system, although it is preferred that the sampling of noise of onboard air conditioning system is conducted first.

In step 4060, the environmental noise in the test site is removed by using the noise of idle system to de=noise the one of the running system. Specifically, the sampled environmental noise waveform is superposed reversely to the one of the onboard air conditioning system to remove the environmental noise therefrom.

In step 4070, the waveform and/or frequency spectrum of the system de-noised in step 4060 is compared with the standard waveform and/or frequency spectrum. In step 4080, the overall performance of the onboard air conditioning system, whether it works normally, is determined based on the comparison result in step 4070. According to an example of the present invention, in step 4080, the performance can also be determined according to the measured temperature at the air outlet of the system in step 4100.

Further, if the overall performance of the onboard air conditioning system is not normal, in step 4090, the failure source and failure cause are determined by the difference between the waveform and/or frequency spectrum of the onboard air conditioning system and the standard waveform and/or frequency spectrum. The de-noised waveform and/or frequency spectrum of the running noise of the system carries the feature of each running device therein. For example, the airflow noise flowing across the heat exchanger has a great difference in frequency from the airflow noise from the compressor, which also renders the frequency spectrum separable to some extent. Further, the change in waveform and/or frequency spectrum is useful in determining the failure cause of the onboard air conditioning system. For example, the running speed of the compressor accelerates when the heat exchanger is blocked, with an increase in sound frequency, either, in this connection, the failure cause of the onboard air conditioning system is determined.

According to an example of the present invention, step 4090 may comprise the following steps:
  a. identify the distinctive waveform and/or frequency spectrum of the device in the onboard air conditioning system from the de-noised waveform and/or frequency spectrum of the running noise thereof, e.g. sound produced when airflow passes through the heat exchanger, sound of a compressor, sound of a turbine and sound of fans;
  b. compare the distinctive waveform and/or frequency spectrum of the device in onboard air conditioning system with the waveform and/or frequency spectrum of the corresponding device in standard waveform and/or frequency spectrum, and obtain the changing patterns of such features as amplitude and frequency of noise of the device therein; e.g. a sudden decrease in amplitude or increase in frequency; and
  c. determine the failure source and failure cause in the system according to one or more change patterns of amplitude and frequency of noise of the device therein. Since a plurality of failures may result in a chain reaction, the use of combined changing patterns of devices therein provides a more accurate failure source and cause.

In an example for the application of the present invention, the microphone is positioned at the air outlet of the onboard air conditioning system in a tested airplane. Activate the system and record each working condition at a length of 5-10 seconds after it runs smoothly, turn down the system and record the environmental sound of the site, then standardize the two types of audio files and de-noise the recorded audio files. Next, save the de=noised waveform files and frequency spectrum files and compare the obtained forms with the standard ones. The result shows a decreased frequency and amplitude in the noise of heat exchanger and an increased frequency in the noise of compressor. Such being the case, there may be a blocking in the heat exchanger in the onboard air conditioning system, one of the most common failures in the system.

In step 4110, compare the waveform and/or frequency spectrum of the noise of onboard air conditioning system de-noised in step 4060 with the history waveform and/or frequency spectrum. In step 4120, determine whether the variation trend of a device therein undergoes a change based on the difference between the waveform and/or frequency spectrum of the noise of the onboard air conditioning system and history ones.

Further, in case that there is a change in the variation trend of the device therein, in step 4130, determine the failure source and failure cause in the onboard air conditioning system according to the difference between the waveform and/or frequency spectrum of the noise of the onboard air conditioning system and history ones.

The de-noised waveform and/or frequency spectrum of the running noise of the system carries the feature of each running device therein. Meanwhile, the difference of variation trend of noise of a specific device resulting from a long-term observation is helpful in determining whether the device enters into a deterioration period.

According to an example of the present invention, step 4030 comprises the following steps:
  a. identify the distinctive waveform and/or frequency spectrum of the device in onboard air conditioning system from the de-noised waveform and/or frequency spectrum of the running noise thereof, e.g. sound produced when airflow passes through the heat exchanger, sound of a compressor, sound of a turbine and sound of fans;
  b. compare the distinctive waveform and/or frequency spectrum of the device in onboard air conditioning system with the waveform and/or frequency spectrum of the corresponding device in standard waveform and/or frequency spectrum, and obtain the changing patterns of such features as amplitude and frequency of noise of the device therein; e.g. an accelerated decrease in amplitude or an accelerated increase in frequency; and
  c. determine whether the device in the system has entered into a deterioration period according to one or more variation trends of amplitude and frequency of noise of the device therein. Likewise, since a plurality of failures may result in a chain reaction, the use of combined changing patterns of devices therein provides a more reliable conclusion.

In step 4140, the time the device breaks down is assessed. That is, the possible time for the malfunction of the device can be assessed if the device therein is in a deterioration period.

According to an example of the present invention, step 4140 comprises the following steps:
  a. determine the limit values of amplitudes or frequencies of the distinctive noises of one or more devices in the onboard air conditioning system when a device breaks down;
  b. extrapolate the change in amplitude or frequency based on the variation trends of amplitudes or frequencies of noises of one or more devices; and
  c. assess the time the amplitudes or frequencies of noises of one or more devices reach limit values based on the extrapolation result.

Clearly, the present invention uses the running noise of the onboard air conditioning system to determine the performance thereof. Also, by comparing waveform and/or frequency spectrum of noise of on board air conditioning system with the waveform and/or frequency spectrum of standard noise or history noise, the present invention allows a detection to short duration failure of the onboard air conditioning system and a long-term monitoring to ensure its stable performance. Instead of installing temperature sensors at the nearly inaccessible positions within the onboard air conditioning system, the present invention provides simply-structured testing equipment that is easy to operate in an airplane.

To obtain the noise during the air conditioner of the airplane operates in a better way and reduce the influence of the background noise, the following approaches may be taken:
  1. Select airport quiet time to make the measurement. For example, the night may be selected to reduce the environment noise because there is fewer or no landing or taking off airplanes and taxiing airplanes or operating vehicles.
  2. Select a quiet place to make the measurement. For example, the hanger or a small airport having fewer airplanes may be used for measurement.
  3. Measure with the APU powered off and using the power from bridge so as to get rid of the APU noise.
  4. Arrange the sound receiving device at a position as near the air conditioner as it can be. According to an embodiment, a microphone can be disposed inside the air conditioner system. For convenience and without change of the airplane, the microphone can be disposed adjacent to the outlet of the air conditioner system under the airplane. Alternatively, the microphone can be disposed adjacent to the inlet of the air conditioner system under the airplane. Since the inlet and outlet of the air conditioner are near each other, the microphone may be arranged between the inlet and outlet of the air conditioner.
  5. Smooth the waveform and frequency spectrum to simulate the real background noise, because the background noise is continuous spectrum.
  6. Keep the standard state during multiple measurements, i.e. use the same state of the air conditioner, including loads, temperature requests, etc, to facilitate the comparison.

Generally, the air conditioner system may have the following faults:
  1. heat exchanger blocking;
  2. foreign mater attached to the blades of compressor;
  3. the blades of the compressor or bearing being damaged; and
  4. degradation of the compressor or turbine thereof.

According to an embodiment of the present invention, the claimed device and method can be used to identify the faults of the air conditioner system. For example, if the heat exchanger is blocked, the turbine will over-rotate, i.e. the rotation speed of the turbine will increase. Consequently, the frequency of the noise generated by friction between the turbine blades and air will increase. This noise is highly identifiable because the rotation speed is quite high and is an important source of the noise of the air conditioner. Another important noise is that generated by friction between the heat exchanger and air, which also is highly identifiable. When the heat exchanger is blocked, the frequency of noise generated by friction between the heat exchanger and air will decrease and the amplitude which reflects energy will increase.

If something is attached to the blades of the turbine, the resistance of rotation will increase and the noise generated by friction between the turbine blades and air will decrease. If the attached is minor things like dust, the decrease is not apparent at the beginning. As time passes and more and more dust becomes attached, the decrease of frequency will become observable.

If the foreign matter attached to the turbine blades impacts the state of high speed rotation status of turbine, and the turbine will become unstable. For example, the turbine blades might draw near to the housing of the compressor, or the air bearing of the turbine might draw near to its holder. If such unstable status deteriorates, the turbine blades might be damaged due to contact with the housing, or the air bearing might be damaged due to contact with its holder. Accordingly, the noise generated by friction between the turbine blades and air will decrease and a new high frequency high energy noise will be found. The device and method of the present invention may be used to identify the unstable status of the turbine through the frequency spectrum and noise waveform and therefore avoid actual damage of the blades or bearing and save high repair expense.

If the compressor or turbine is degraded, a usual result is decrease of turbine rotation speed, which result in the noise generated by friction between the turbine blades and air decreased. However, it is a slow change. By comparison of the noise spectrums at different times, this change will be identified. Consequently the air conditioner may be repaired before failure.

Such condition based repair can also save a lot repair expense.

The above examples are only used to describe, rather than limit, the present invention. A person skilled in the art can make various changes to and modify the forms of the present invention without departing from the scope thereof. In other words, all equivalent technical solutions fall under the present invention.

I claim:

1. A testing equipment of an airplane air conditioning system, comprising:
   a sound receiver, and
   a sound processor, wherein the sound processor processes running noise of the airplane air conditioning system sampled by the sound receiver to assess the operative condition of the system,
   wherein the sound receiver samples environmental noise when the airplane air conditioning system is not running, and wherein the sound processor de-noises the running noise by using the environmental noise; and
   the sound processor assesses whether the plurality of devices are in a deterioration period by analyzing changes in variation trends of waveforms and/or frequency spectrums of the running noises of the plurality of devices in the airplane air conditioning system.

2. The testing equipment according to claim 1, wherein the sound receiver is an independent microphone or a built-in microphone.

3. The testing equipment according to claim 1, wherein the sound receiver is mounted at the air outlet of the airplane air conditioning system or in the cabin.

4. The testing equipment according to claim 1, wherein the sound processor determines a change in the running noise by comparing the running noise with a standard noise of the airplane air conditioning system.

5. The testing equipment according to claim 1, wherein the sound processor assesses a failure source of the airplane air conditioning system.

6. The testing equipment according to claim 5, wherein the sound processor assesses a failure cause of the airplane air conditioning system.

7. The testing equipment according to claim 5, wherein the sound processor analyzes a waveform and/or frequency spectrum of the running noise of the airplane air conditioning system, and extracts waveforms and/or frequency spectrums of noises corresponding to a plurality of devices in the airplane air conditioning system.

8. The testing equipment according to claim 7, wherein the sound processor determines the failure source or failure cause by a combined use of the waveforms and/or frequency spectrums of noises of the plurality of devices.

9. The testing equipment according to claim 1, wherein the sound processor analyzes changes in variation trends of waveforms and/or frequency spectrums of the running noises of the plurality of devices in the airplane air conditioning system by comparing the running noise with history noises of the airplane air conditioning system.

10. The testing equipment according to claim 1, wherein the sound processor assesses a time of failure of the plurality of devices.

11. A method of testing the airplane air conditioning system, comprising:
    sampling a running noise of the airplane air conditioning system,
    sampling an environmental noise when the airplane air conditioning system is not running;
    denoising the running noise by using the environmental noise;
    assessing an operative condition of the airplane air conditioning system; and
    assessing whether the plurality of devices are in a deterioration period by analyzing changes in variation trends of waveforms and/or frequency spectrums of the running noises of the plurality of devices in the airplane air conditioning system.

12. The method according to claim 11, further comprises determining a change in the running noise by comparing the running noise with the standard noise of the airplane air conditioning system.

13. The method according to claim 11, further comprises assessing a failure source of the airplane air conditioning system.

14. The method according to claim 11, further comprises assessing a failure cause of the airplane air conditioning system.

15. The method according to claim 11, further comprises analyzing waveform and/or frequency spectrum of the running noise of the airplane air conditioning system, and extracting the waveforms and/or frequency spectrums of noises corresponding to a plurality of devices in the airplane air conditioning system.

16. The method according to claim 11, further comprises determining a failure source or failure cause by a combined use of waveforms and/or frequency spectrums of noises of a plurality of devices.

17. The method according to claim 11, wherein analyzing changes in variation trends of waveforms and/or frequency spectrums of the running noises of the plurality of devices in the airplane air conditioning system comprises analyzing changes in variation trends of waveforms and/or frequency spectrums of the running noises of the plurality of devices in the airplane air conditioning system by comparing the running noise with history noises of the airplane air conditioning system.

18. The method according to claim 11, further comprises assessing a time of failure of the plurality of devices.

* * * * *